United States Patent
Watanabe et al.

(10) Patent No.: US 10,736,498 B2
(45) Date of Patent: Aug. 11, 2020

(54) SPECIAL LIGHT ENDOSCOPE

(71) Applicant: OLYMPUS CORPORATION, Tokyo (JP)

(72) Inventors: Yoshihiko Watanabe, Yokohama (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 15/828,503

(22) Filed: Dec. 1, 2017

(65) Prior Publication Data
US 2018/0084980 A1    Mar. 29, 2018

Related U.S. Application Data

(63) Continuation of application No. PCT/JP2015/065945, filed on Jun. 2, 2015.

(51) Int. Cl.
*A61B 1/00* (2006.01)
*A61B 1/04* (2006.01)
(Continued)

(52) U.S. Cl.
CPC ............ *A61B 1/04* (2013.01); *A61B 1/00009* (2013.01); *A61B 1/06* (2013.01); *A61B 1/0638* (2013.01);
(Continued)

(58) Field of Classification Search
None
See application file for complete search history.

(56) References Cited

U.S. PATENT DOCUMENTS 5,850,496 A * 12/1998 Bellahsene ........ A61B 1/00117
385/117
2013/0245410 A1 * 9/2013 Saito .................. A61B 1/00009
600/339
(Continued)

FOREIGN PATENT DOCUMENTS

JP    2009-297313 A    12/2009
JP    2012-152332 A    8/2012
(Continued)

OTHER PUBLICATIONS

English translation of JP 2012-152332 (2012).*
(Continued)

*Primary Examiner* — Timothy J Neal
(74) *Attorney, Agent, or Firm* — Scully, Scott, Murphy & Presser, P.C.

(57) ABSTRACT

An endoscope includes an illuminator to emit illumination light comprised by narrow band lights different in wavelength from an end portion of the endoscope and an imager to image an observation object illuminated by the illumination light emitted from the illuminator. The illuminator includes a light quantity output adjuster to independently control the light quantity of each of the narrow band lights. The endoscope allows observation in three types of modes of a white light mode, a special light mode, and a hybrid mode. A spectral pattern of illumination light in the hybrid mode includes at least a part of a color region of a narrow band light included in the special light mode and is different from either of a spectral pattern of illumination light in the white light mode and a spectral pattern of illumination light in the special light mode.

21 Claims, 9 Drawing Sheets

(51) Int. Cl.
  *G02B 23/24* (2006.01)
  *A61B 1/06* (2006.01)
  *G02B 27/10* (2006.01)

(52) U.S. Cl.
  CPC ........ *A61B 1/0669* (2013.01); *G02B 23/2461* (2013.01); *G02B 23/2469* (2013.01); *A61B 1/00039* (2013.01); *A61B 1/00096* (2013.01); *G02B 27/1006* (2013.01)

(56) References Cited

U.S. PATENT DOCUMENTS

| 2015/0092033 A1* | 4/2015 | Kuramoto | H04N 9/045 348/68 |
| 2015/0342448 A1 | 12/2015 | Asatori | |

FOREIGN PATENT DOCUMENTS

| JP | 2013-188365 A | 9/2013 |
| JP | 2014-150932 A | 8/2014 |
| JP | 2015-066131 A | 4/2015 |
| JP | 2015-085097 A | 5/2015 |
| WO | 2014/192563 A1 | 12/2014 |

OTHER PUBLICATIONS

Japanese Office Action dated Nov. 13, 2018 in Japanese Patent Application No. 2017-521403.
Chinese Office Action dated Nov. 2, 2018 in Chinese Patent Application No. 201580080598.2.
International Search Report dated Jun. 30, 2015 issued in PCT/JP2015/065945.
English translation of International Preliminary Report on Patentability dated Dec. 14, 2017 together with the Written Opinion received in related International Application No. PCT/JP2015/065945.

* cited by examiner

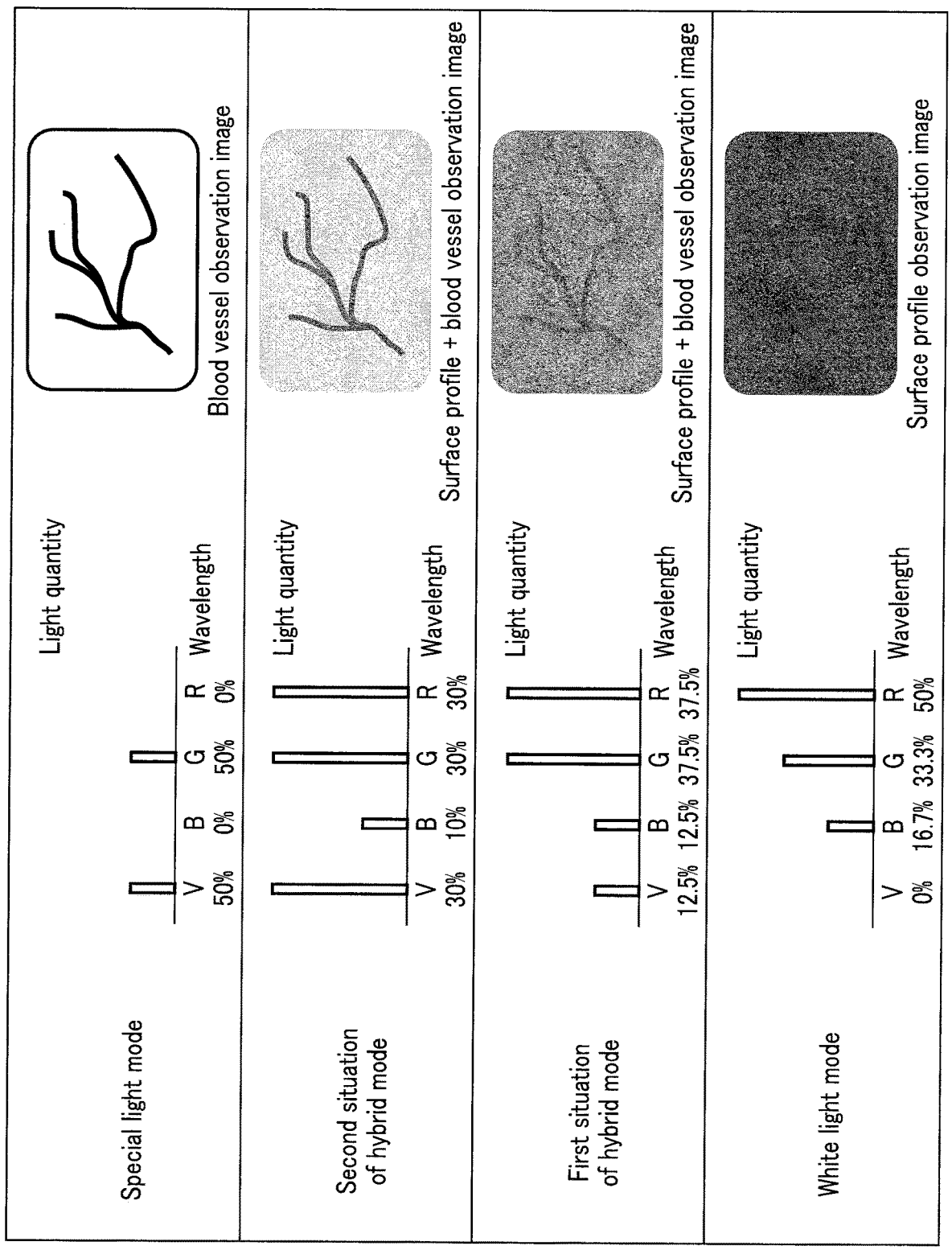
F I G. 4

SPECIAL LIGHT ENDOSCOPE

CROSS REFERENCE TO RELATED APPLICATIONS

This application is a Continuation application of PCT Application No. PCT/JP2015/065945, filed Jun. 2, 2015, the entire contents of which are incorporated herein by reference.

BACKGROUND OF THE INVENTION

1. Field of the Invention

The present invention relates to a special light endoscope.

2. Description of the Related Art

At present, as the observation and identification of a lesion by an endoscope, first, a rough screening observation of a surface is made with white light to identify a suspected area to a certain degree, and after that, the suspected area is magnified for detailed observation of vascular abnormalities, etc. with a special kind of light for narrow band light observation etc.

In that case, illumination light is switched between white light and special light for each of the case of rough surface observation by screening and the case of detailed observation by magnification.

BRIEF SUMMARY OF THE INVENTION

An endoscope includes an illuminator to emit illumination light comprised by narrow band lights different in wavelength from an end portion of the endoscope and an imager to image an observation object illuminated by the illumination light emitted from the illuminator. The illuminator includes a light quantity output adjuster to independently control light quantity of each of the narrow band lights. The endoscope allows observation in three types of modes of a white light mode, a special light mode, and a hybrid mode. The illuminator, in the hybrid mode, emits illumination light in a spectral pattern that includes at least a part of a color region of a narrow band light included in the special light mode and is different from either of a spectral pattern of illumination light in the white light mode and a spectral pattern of illumination light in the special light mode.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 schematically shows the combination of the spectral pattern of illumination light and a display image on a monitor in each of the white light mode, the special light mode, and a situation in the hybrid mode.

FIG. 3 schematically shows an example of the combination of a spectral pattern and a display image on a monitor in each of the white light mode, the special light mode, and first and second situations in the hybrid mode.

FIG. 4 schematically shows another example of the combination of a spectral pattern and a display image on a monitor in each of the white light mode, the special light mode, and first and second situations in the hybrid mode.

DETAILED DESCRIPTION OF THE INVENTION

Figure 1:
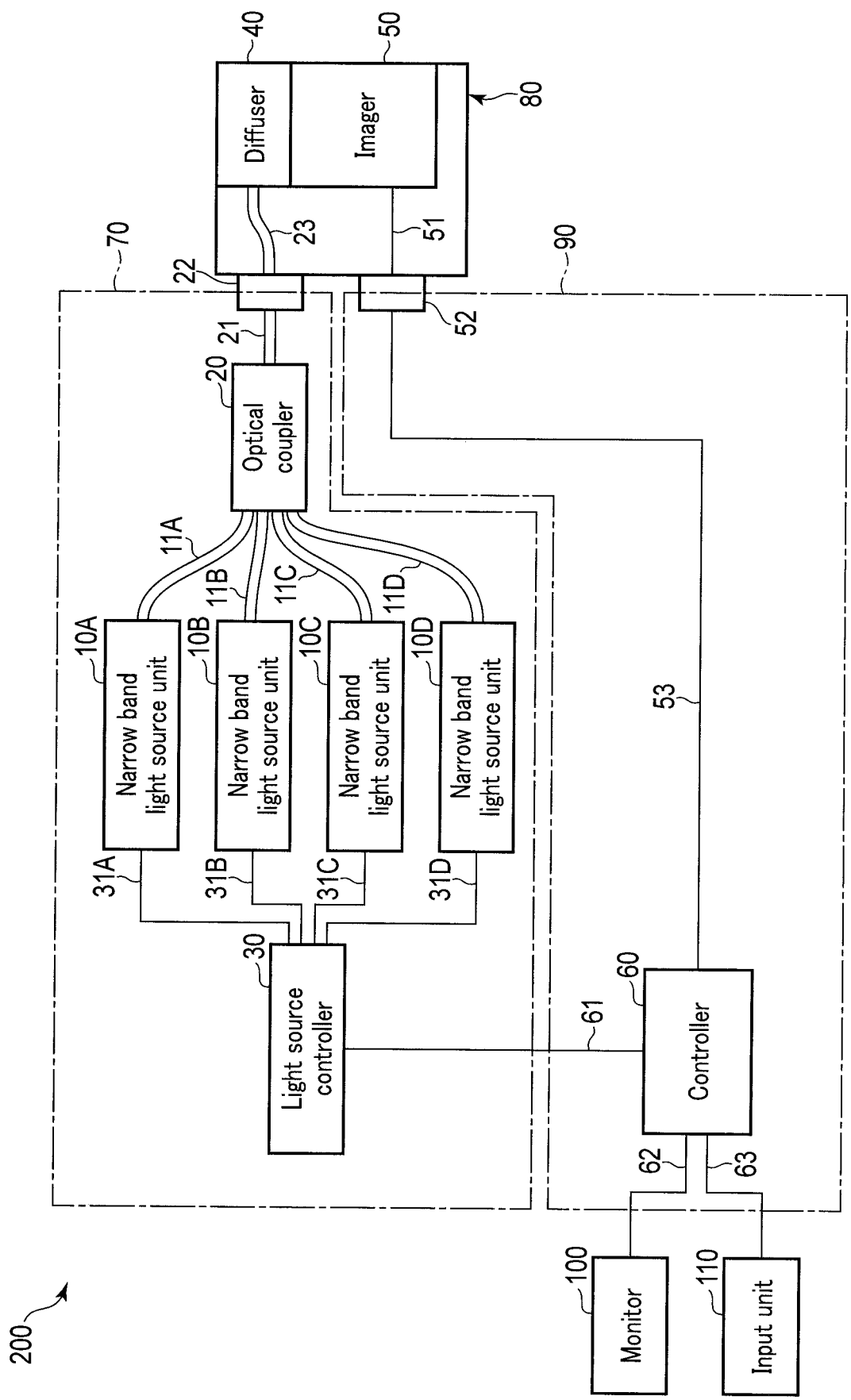
FIG. 1 is a block diagram of a special light endoscope according to an embodiment.

As shown in FIG. 1, a special light endoscope 200 in the present embodiment includes a light source apparatus 70 that generates illumination light to output it, an insertion portion 80 that is inserted into a hollow of a subject, radiating illumination light from a light source apparatus 70 to an observation object, so as to image the observation object, generating its image signal to output it, an image processing apparatus 90 that processes an image signal from the insertion portion 80 to generate an image, a monitor 100 that displays an image generated by the image processing apparatus 90, and an input unit 110 that accepts an input operation.

The insertion portion 80 is connected to the light source apparatus 70 and the image processing apparatus 90 through a connector 22 and a connector 52, respectively, in a manner freely attachable and detachable.

The light source apparatus 70 includes a narrow band light source unit 10A having the chromaticity of red, a narrow band light source unit 10B having the chromaticity of green, a narrow band light source unit 10C having the chromaticity of blue, a narrow band light source unit 10D having the chromaticity of violet, and a light source controller 30 that is electrically connected to the narrow band light source units 10A, 10B, 10C, and 10D through interconnect lines 31A, 31B, 31C, and 31D, respectively, so as to independently control the emission light quantity of each of the narrow band light source units 10A, 10B, 10C, and 10D, an optical coupler 20 that is optically connected to the narrow band light source units 10A, 10B, 10C, and 10D through optical fibers 11A, 11B, 11C, and 11D, respectively, so as to couple light emitted from the narrow band light source units 10A, 10B, 10C, and 10D to produce illumination light, and an optical fiber 21 that guides illumination light to the insertion portion 80.

The insertion portion 80 includes an optical fiber 23 that is optically connected to the optical fiber 21 of the light source apparatus 70 through the connector 22, a diffuser 40 that emits illumination light guided by the optical fiber 23 to diffuse from the tip end of the insertion portion 80 to the observation object, an imager 50 such as a CCD that two-dimensionally receives light from the observation object at the tip end of the insertion portion 80, and an image cable 51 for transmitting an electrical signal of the imager 50 to the image processing apparatus 90.

The image processing apparatus 90 comprises an image cable 53 that is electrically connected to the image cable 51 of the insertion portion 80 through the connector 52, and a controller 60 that processes an image signal provided through the image cable 53 from the imager 50. The monitor 100 that outputs a processed image etc. is electrically connected to the controller 60 through an interconnect line 62. In addition, the input unit 110 that gives instructions on image processing etc. is electrically connected to the controller 60 through an interconnect line 63. The controller 60, which is electrically connected to the light source controller 30 of the light source apparatus 70 through an interconnect line 61, controls the light source controller 30 according to instructions from the input unit 110.

The narrow band light source unit 10A emits a narrow band light having a wavelength included in the red wavelength region. The narrow band light source unit 10B emits a narrow band light having a wavelength included in the green wavelength region. The narrow band light source unit 10C emits a narrow band light having a wavelength included in the blue wavelength region. The narrow band light source unit 10D emits a narrow band light having a wavelength included in the violet wavelength region.

Specifically, the narrow band light source unit 10A emits a narrow band light having a wavelength included in the wavelength region of 570 through 780 nm. The narrow band light source unit 10B emits a narrow band light having a wavelength included in the wavelength region of 500 through 570 nm. The narrow band light source unit 10C emits a narrow band light having a wavelength included in the wavelength region of 450 through 500 nm. The narrow band light source unit 10D emits a narrow band light having a wavelength included in the wavelength region of 380 through 450 nm.

The narrow band light source unit 10B may emit a narrow band light having a wavelength included in the wavelength region of 510 through 550 nm, for example. Alternatively, the narrow band light source unit 10B may emit a narrow band light having a wavelength included in the wavelength region of 530 through 550 nm, which is the green wavelength region. The narrow band light source unit 10D may emit a narrow band light having a wavelength included in the wavelength region of 380 through 445 nm, for example. Alternatively, the narrow band light source unit 10D may emit a narrow band light having a wavelength included in the wavelength region of 390 through 445 nm, which is the violet wavelength region.

Each of the narrow band light source units 10A, 10B, 10C, and 10D may be constituted by a single narrow band light source, for example. However, it is not limited to this; each of the narrow band light source units 10A, 10B, 10C, and 10D may be constituted by narrow band light sources. A narrow band light source may be constituted by a laser, for example. However, it is not limited to this; a narrow band light source may be constituted by a light source whose wavelength width is around 10 through 20 nm, such as an LED.

The emission light quantity of each of the narrow band light source units 10A, 10B, 10C, and 10D can arbitrarily be independently controlled by the light source controller 30.

The optical fibers 11A, 11B, 11C, 11D, 21, and 23 are constituted by multi-mode fibers. As an example, a fine fiber with a core diameter of 105 μm, a cladding diameter of 125 μm, and a diameter that includes a protection layer to be an outer coat of around φ0.3 through 0.5 mm can be used.

The special light endoscope 200 in the present embodiment allows an observation object to be observed in three types of modes of a white light mode, a special light mode, and a hybrid mode. The three types of modes are exclusive of one another. The white light mode is a mode to radiate illumination light appropriate for surface observation of an observation object, so as to make observation with a display image in white. In the white light mode, it is appropriate that a display image in white, which is the natural color of an observation object observed when being illuminated with illumination light such as sunlight, is reproduced, and the illumination light does not need to be white. The special light mode is a mode to radiate illumination light of a special light appropriate for blood vessel observation, so as to make an observation. The hybrid mode is a mode to radiate illumination light that includes at least a part of a color region of a narrow band light included in the special light mode and is different from either of illumination light in the white light mode and illumination light in the special light mode, so as to make an observation.

Accordingly, the light source apparatus 70, in the hybrid mode, emits illumination light in a spectral pattern that includes at least a part of a color region of a narrow band light included in the special light mode, and is different from either of a spectral pattern of illumination light in the white light mode and a spectral pattern of illumination light in the special light mode.

For example, the light source apparatus 70, in the hybrid mode, selectively emits illumination light having a first spectral pattern close to the spectral pattern of illumination light in the white light mode, and illumination light having a second spectral pattern close to the spectral pattern of illumination light in the special light mode. For example, the second spectral pattern retains a color tone almost equal to a color tone of the first spectral pattern, and differs from the first spectral pattern in the light quantity of each narrow band light except in a visible light region.

Here, "retaining almost equal the color tone" means that, for example, the value of ΔE widely used as the most standard color-difference formula in the CIE 1976 L*a*b* colorimetric system is less than or equal to ten, preferably less than or equal to three.

In addition, the light source apparatus 70, in the hybrid mode, emits illumination light including a narrow band light included in common in illumination light in the white light mode and that in the special light mode. The light quantity of the narrow band light included in common is the light quantity between the light quantity of each narrow band light of illumination light in the white light mode and the light quantity of each narrow band light of illumination light in the special light mode.

In addition, the light source apparatus 70, in the hybrid mode, emits illumination light that has the light quantity between the light quantity of each narrow band light of illumination light in the white light mode, and the light quantity of each narrow band light of illumination light in the special light mode.

In addition, the light source apparatus 70, in the hybrid mode, emits illumination light constituted of narrow band lights that each have the light quantity of an average of the light quantity of each narrow band light of illumination light in the white light mode and the light quantity of each narrow band light of illumination light in the special light mode.

The light source apparatus 70, in the white light mode, emits illumination light that includes at least a narrow band light in each of at least two color regions of red (R), green (G), and blue (B) in the special light mode, emits illumination light that includes at least a narrow band light in at least either of the region of green (G) and the region of violet (V), and in the hybrid mode, emits illumination light that includes at least a narrow band light in each of color regions including narrow band lights included in illumination light in the white light mode and a color region including a narrow band light included in illumination light in the special light mode and in which the light quantity of each narrow band light in color regions other than the color region including a narrow band light included in illumination light in the special light mode is large compared to the special light mode.

For example, the light source apparatus 70, in the white light mode, emits illumination light that includes at least a narrow band light in each of the regions of red (R), green (G), and blue (B) in the special light mode, emits illumination light that includes at least a narrow band light in at least either of the region of green (G) and the region of violet (V), and in the hybrid mode, emits illumination light that includes at least a narrow band light in each of the regions of red (R), green (G), blue (B), and violet (V) and in which the light quantity of each narrow band light in color regions not included in illumination light in the special light mode is enhanced.

In addition, the light source apparatus 70, in the hybrid mode, emits illumination light in which the light quantity of a narrow band light in the bluish-violet region of 380 through 500 nm in wavelength is large compared to illumination light in the white light mode and that retains a color tone closer to illumination light in the white light mode than that in the special light mode. For example, the light source apparatus 70, in the hybrid mode, emits illumination light in which the light quantity of a narrow band light in the bluish-violet region of 380 through 500 nm in wavelength is large compared to illumination light in the white light mode and that retains a color tone almost equal to illumination light in the white light mode. Furthermore, the light source apparatus 70, in the hybrid mode, adjusts the light quantity of a narrow band light in the yellowish-red region so as to maintain the color tone.

The light source apparatus 70, in the hybrid mode, emits illumination light in which the light quantity of a narrow band light in the greenish-yellow region of 500 through 570 nm in wavelength is large compared to illumination light in the white light mode and that retains a color tone almost equal to illumination light in the white light mode. Furthermore, the light source apparatus 70, in the hybrid mode, adjusts the light quantity of a narrow band light in each of the red and blue regions so as to maintain the color tone.

The light source apparatus 70, in the special light mode, emits illumination light that includes at least a narrow band light in at least each of the wavelength region of 380 through 445 nm and that of 510 through 550 nm, and in the white light mode, emits illumination light that includes at least a narrow band light in at least each of a wavelength region of 380 through 500 nm, a wavelength region of 500 through 570 nm, and a wavelength region of 570 through 700 nm.

The light source apparatus 70, in the special light mode, emits illumination light that includes at least a narrow band light in at least each of the wavelength region of 390 through 445 nm that is violet, and a wavelength region of 530 through 550 nm that is green.

Figure 2:
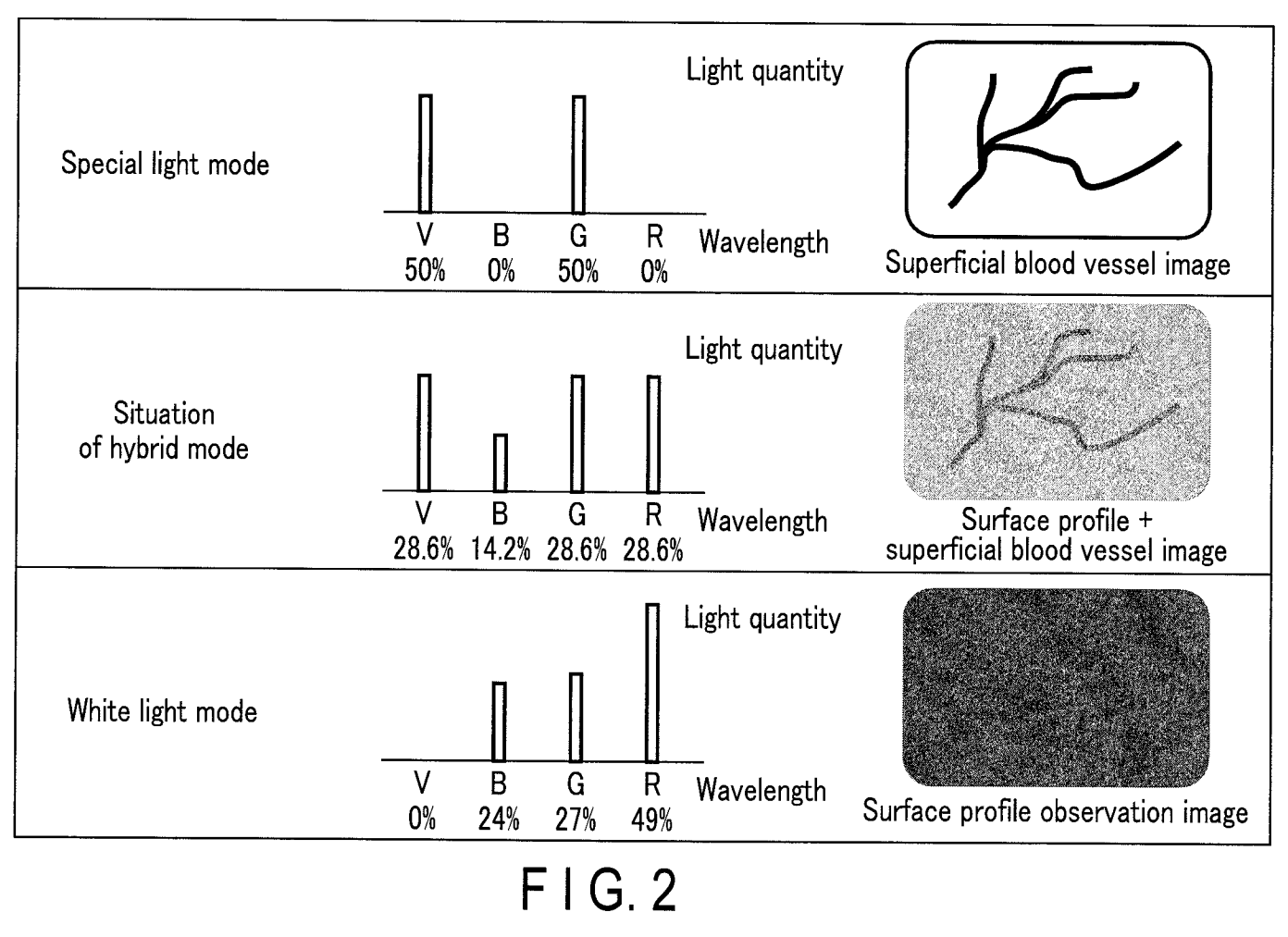

FIG. 2 schematically shows the combination of the spectral pattern of illumination light and a display image on a monitor in each of the white light mode, the special light mode, and a situation in the hybrid mode.

Illumination light in the white light mode, which is white light appropriate for surface observation, has a single narrow band light in each of the wavelength regions of red, green, and blue. Here, a white color, in its broad sense, includes white colors that are strictly off a color tone of white, such as a white in which a color tone of red is slightly high and a white in which a color tone of blue is slightly high.

White light is produced by controlling the narrow band light source units 10A, 10B, and 10C so that the light quantity ratio of red light (R) emitted from the narrow band light source unit 10A, green light (G) emitted from the narrow band light source unit 10B, and blue light (B) emitted from the narrow band light source unit 10C is a predefined value. In the white light mode, the narrow band light source unit 10D does not necessarily need to be stopped. If the light quantity of violet light (V) emitted from the narrow band light source unit 10D is a little, for example, less than or equal to 1/20 of the light quantity of red light (R), the illumination light may be regarded as substantially white light.

Illumination light in the special light mode, which is special light appropriate for blood vessel observation, has a single narrow band light in each of the wavelength region of 380 through 500 nm and that of 500 through 570 nm, whose light quantity is appropriately controlled according to a subject. Preferable special light, which is used for narrow band light observation (Narrow Band Imaging, NBI) using violet light and green light, has a single narrow band light in each of the wavelength region of 390 through 445 nm, which is a violet wavelength region, and the wavelength region of 530 through 550 nm, which is a green wavelength region.

Special light is produced by controlling the narrow band light source units 10B and 10D so that the light quantity ratio of green light (G) emitted from the narrow band light source unit 10B to violet light (V) emitted from the narrow band light source unit 10D is a predefined value. In the special light mode, the narrow band light source units 10A and 10C do not necessarily need to be stopped. For example, if the light quantity of red light (R) emitted from the narrow band light source unit 10A is a little, for example, less than or equal to 1/20 of the light quantity of green light (G) or violet light (V), illumination light may be regarded as substantially special light. The same is true of blue light (B) emitted from the narrow band light source unit 10C.

Illumination light in the hybrid mode, which is light different from either of white light and special light, is produced by controlling the narrow band light source units 10A, 10B, 10C, and 10D so that the light quantity ratio of red light (R) emitted from the narrow band light source unit 10A, green light (G) emitted from the narrow band light source unit 10B, blue light (B) emitted from the narrow band light source unit 10C, to violet light (V) emitted from the narrow band light source unit 10D is a value different from either of the light quantity ratio in white light and the light quantity ratio in special light.

This light quantity ratio does not necessarily need to be a pair of fixed values, and, for example, may be switched among pairs of fixed values. Alternatively, four numerical values that determine the light quantity ratio may be independently changed gradually or continuously. Such designation, switching, or changing of the light quantity ratio is performed according to instructions from the input unit 110. Because of this, the input unit 110 may include an interface for designating or arbitrarily changing the emission light quantity of each of the narrow band light source units 10A, 10B, 10C, and 10D.

In FIG. 2, a situation in the hybrid mode in which the light quantity ratio is a pair of fixed values is shown. The spectral pattern of illumination light in this situation in the hybrid mode is different from either of a spectral pattern of illumination light in the white light mode and a spectral pattern of illumination light in the special light mode. In more detail, in the spectral pattern of illumination light in this situation in the hybrid mode, compared to the spectral pattern of white light, the light quantity of each of green light (G) and violet light (V) dominantly included in special light is enhanced. From another perspective, the spectral pattern of illumination light in this situation in the hybrid mode may also be said to be an intermediate between the spectral pattern of illumination light in the white light mode and the spectral pattern of illumination light in the special light mode.

In the white light mode, as an image displayed on the monitor 100, a surface profile observation image of an observation object is well projected; however, no blood vessel image of the observation object is projected. However, in the special light mode, as an image displayed on the monitor 100, a blood vessel image of an observation object is well projected; however, no surface profile observation image of the observation object is projected. In contrast, in this situation in the hybrid mode, as an image displayed on the monitor 100, a surface profile observation image of an observation object is projected, and a blood vessel image of the observation object is also projected.

Figure 3:
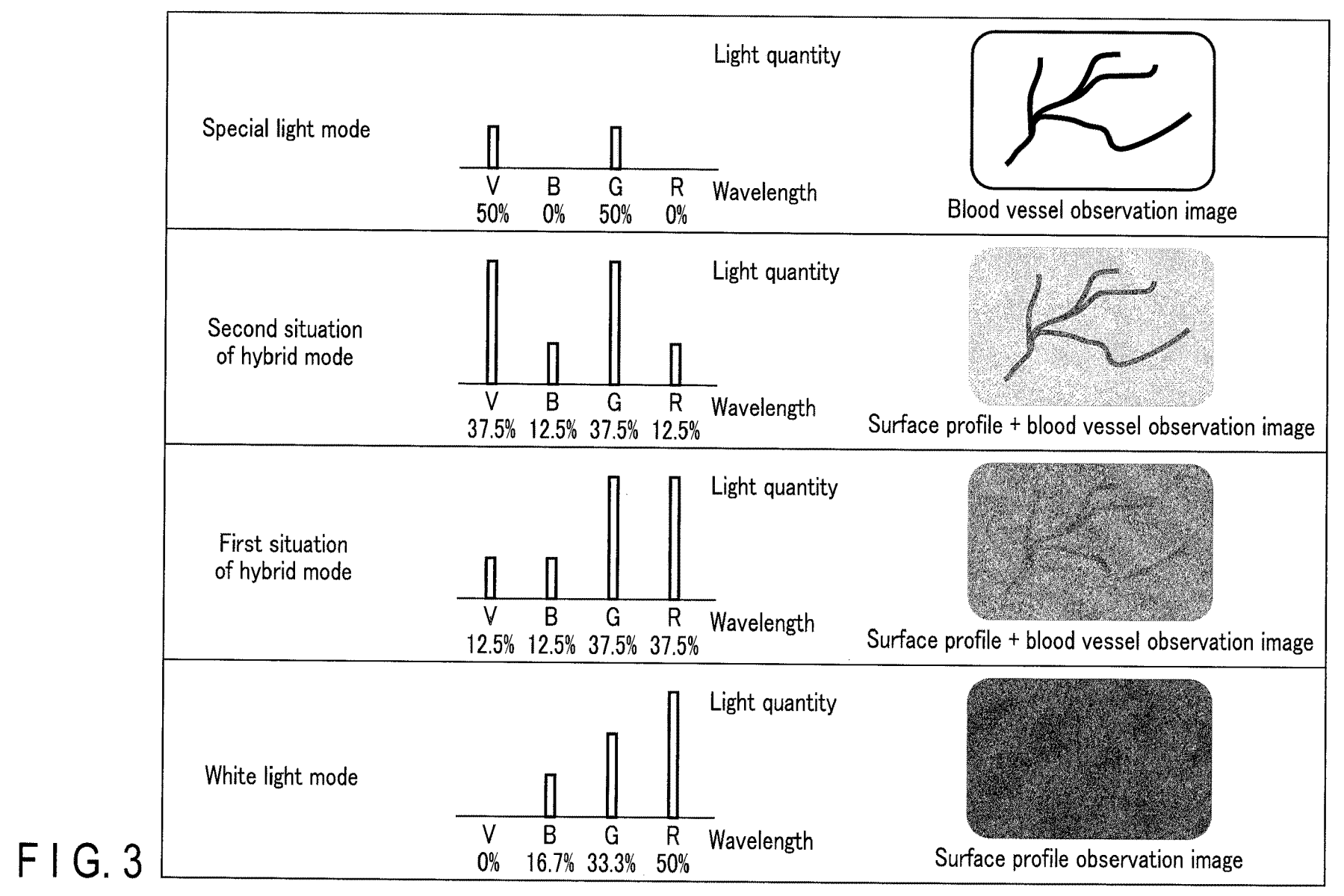

FIG. 3 schematically shows an example of the combination of a spectral pattern and a display image on a monitor in each of the white light mode, the special light mode, and first and second situations in the hybrid mode.

In this observation case, the hybrid mode is switchable between the first and second situations, in which the light quantity ratios differ from each other. That is, the light source apparatus 70, in the hybrid mode, can selectively emit illumination light having a first spectral pattern, and illumination light having a second spectral pattern different from the first spectral pattern.

In the white light mode, the light quantity ratio of red light (R), green light (G), blue light (B), and violet light (V) is set to 3:2:1:0. In this case, an image appropriate for surface screening is obtained.

In the first situation in the hybrid mode, the light quantity ratio of red light (R), green light (G), blue light (B), and violet light (V) is set to 3:3:1:1. In this case, illumination light is basically white light appropriate for surface screening. However, since green light and violet light capable of blood vessel observation are slightly added, an image in which a blood vessel image is thinly overlapped on a surface profile image is obtained. That is, observation with this illumination light may be said to be an observation that is close to observation with white light, which weights the purpose for rough surface observation by screening of a lesion.

In the second situation in the hybrid mode, the light quantity ratio of red light (R), green light (G), blue light (B), and violet light (V) is set to 1:3:1:3. The spectral pattern of illumination light in this second situation in the hybrid mode is close to the spectral pattern of illumination light in the special light mode, compared to the spectral pattern of illumination light in the first situation in the hybrid mode. In this case, the light quantity of each of violet and green is large, while a little bit of white light is retained. Thus, compared to the first situation in the hybrid mode, an image closer to special light appropriate for blood vessel observation is obtained. That is, an observation with this illumination light may be said to be an observation close to the observation with special light, which weights the purpose for detailed observation of a lesion.

The closeness of the spectral pattern of illumination light is determined by the ratio (proportion) of the light quantity of each wavelength accounting for aggregate light quantity (total light quantity of red light, green light, blue light, and violet light). For example, according to the light quantity ratio of each color in the spectral pattern in the white light mode and that in the first situation in the hybrid mode in FIG. 3, the light quantity percentages of red light (R) and green light (G) in the white light mode are 50% and 33.3%, respectively, and at least equal to or greater than around twice as high as the light quantity percentages of blue light (B) and violet light (V), i.e. 16.7% and 0%. Accordingly, the relationship of the light quantity of red light and the light quantity of green light being greater>the light quantity of blue light and the light quantity of violet light holds true.

Next, in the first situation in the hybrid mode, the light quantity percentages of red light (R) and green light (G) are both 37.5%, and around three times as large as the light quantity percentages of blue light (B) and violet light (V), i.e. 12.5%. Accordingly, as in the white light mode, the relationship of the light quantity of red light and the light quantity of green light>the light quantity of blue light and that of violet light holds up.

Meanwhile, in the second situation in the hybrid mode, the relationship of the light quantity of green light and the light quantity of violet light>the light quantity of red light and the light quantity of blue light is derived.

As discussed above, the spectral pattern in the first situation in the hybrid mode may be determined to be closer to the spectral pattern in the white light mode than the spectral pattern in the second situation in the hybrid mode.

In the special light mode, the light quantity ratio of red light (R), green light (G), blue light (B), and violet light (V) is set to 0:1:0:1. In this case, an image appropriate for blood vessel observation is obtained.

By switching among the white light mode, the hybrid mode, and the special light mode in order, after the screening of an observation object, and efficient, correct screening of a suspected part, observation of a lesion is performed.

FIG. 4 schematically shows another example of the combination of a spectral pattern and a display image on a monitor in each of the white light mode, the special light mode, and first and second situations in the hybrid mode.

In this observation case, the light quantity percentages of red light (R), green light (G), blue light (B), and violet light (V) in the white light mode, and the light quantity percentages of red light (R), green light (G), blue light (B), and violet light (V) in the special light mode are the same as those in the observation case of FIG. 3.

In this observation case, as in the observation case of FIG. 3, the hybrid mode is switchable between the first and second situations in which the light quantity ratios differ from each other. That is, the light source apparatus 70, in the hybrid mode, can selectively emit illumination light having a first spectral pattern, and illumination light having a second spectral pattern different from the first spectral pattern.

In this observation case, in the first situation in the hybrid mode, the light quantity ratio of red light (R), green light (G), blue light (B), and violet light (V) is set to 1:1:3:3. In addition, in the second situation in the hybrid mode, the light quantity ratio of red light (R), green light (G), blue light (B), and violet light (V) is set to 3:1:3:3. That is, in the first and second spectral patterns, the light quantity ratio of red light (R), green light (G), and blue light (B) is the same, and only the light quantity of violet light (V) is different.

Since the light quantity ratios of the first and second spectral patterns are set in such a manner, when illumination light of the first spectral pattern is switched to illumination light of the second spectral pattern, for example, only the light quantity of violet light (V) is changed without any change in the light quantity of each of red light (R), green light (G), and blue light (B). Accordingly, there is no change in the color tone of an observation image, and blood vessels are easily seen. At the time of switching of illumination light, the light quantity of each of red light (R), green light (G), and blue light (B) may be changed with its light quantity ratio maintained constant.

Figure 5:
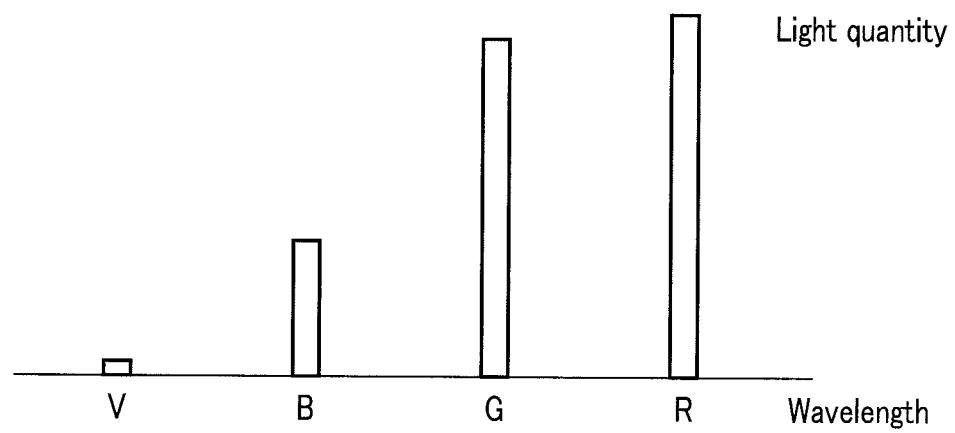
FIG. 5 shows an example of the spectral pattern of illumination light in the hybrid mode.

FIG. 5 shows an example of the spectral pattern of illumination light in the hybrid mode.

In this example, illumination light is basically of the color tone of white light, in which the light quantity of green light being 530 nm in wavelength is increased. Accordingly, an image made in which an image of observation of deep blood vessels is overlapped on an image appropriate for screening is obtained.

Figure 6:
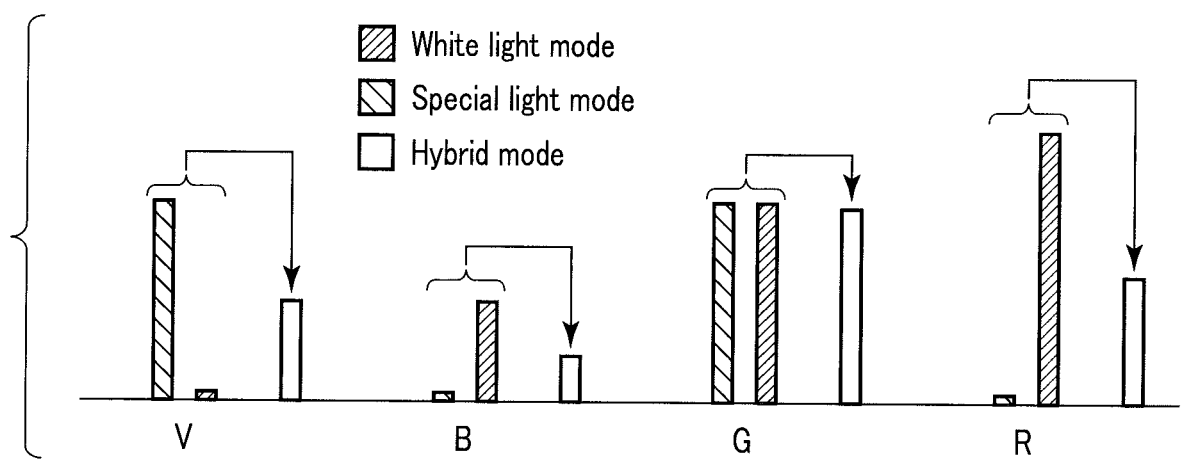
FIG. 6 shows another example of the spectral pattern of illumination light in the hybrid mode.

FIG. 6 shows another example of the spectral pattern of illumination light in the hybrid mode.

In this example, illumination light is constituted of narrow band lights that each have the light quantity of an average of the light quantity of each narrow band light in the white light mode and the light quantity of each narrow band light in the special light mode. In other words, the light quantity ratio of the narrow band lights of illumination light in the hybrid mode is the ratio of the added numerical values of the light quantity ratio of narrow band lights of illumination light in the special light mode and the light quantity ratio of narrow band lights of illumination light in the white light mode.

Figure 7:
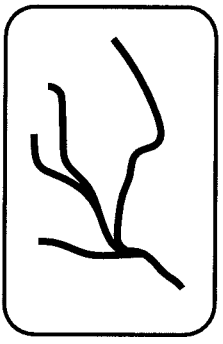
FIG. 7 schematically shows another example of the combination of a spectral pattern of illumination light and a display image on a monitor in each of the white light mode, the special light mode, and a situation in the hybrid mode.

The white light mode may also be achieved by generating white light by use of two lights of different colors of red light (R), green light (G), and blue light (B). FIG. 7 shows an example of the achievement of the white light made by lights of two colors of red light (R) and blue light (B). In the white light mode of this observation case, the light quantity percentages of red light (R), green light (G), and blue light (B) are 51%, 0% and 49%, respectively. For example, red light (R) may be light of 600 nm in wavelength, and blue light (B) may be light of 490 nm in wavelength. The color tone in this case is, according to a CIE Chromaticity Diagram (CIE 1931), the center of the straight line connecting these wavelengths of two colors, and white.

Next, the method of switching the modes will be explained. In the following explanation, the first and second situations in the hybrid mode are respectively referred to as hybrid mode 1 and hybrid mode 2 for convenience and each situation is regarded as a mode.

Figure 8:
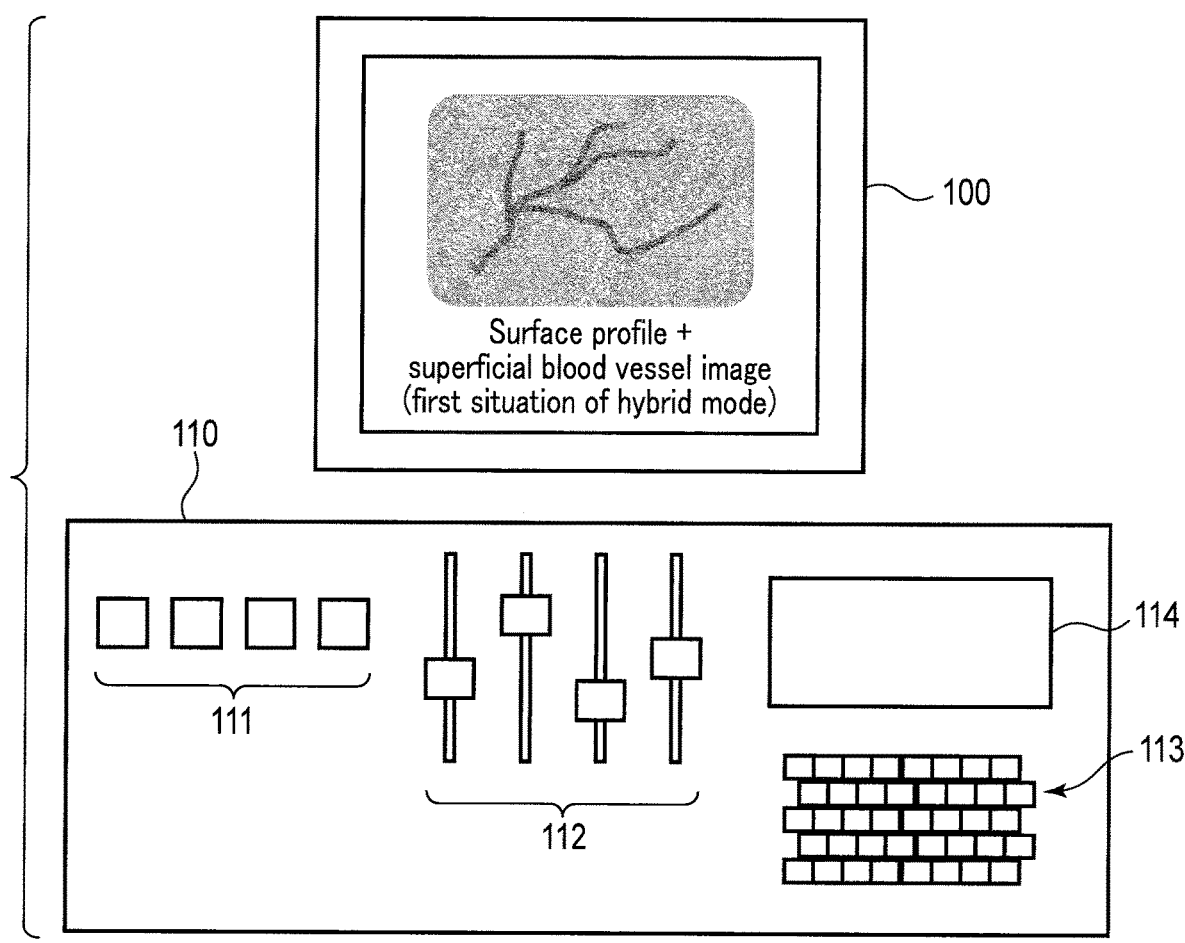
FIG. 8 shows the configuration of the input unit shown in FIG. 1.

FIG. 8 shows the configuration of the input unit 110. The input unit 110 includes observation mode selecting switches 111 for selecting an observation mode, light quantity adjusting switches 112 for adjusting light quantity, input keys 113 for inputting information, and a display panel 114 for displaying inputted information.

The observation mode selecting switches 111 are constituted of four buttons corresponding to the white light mode, the special light mode, and hybrid modes 1 and 2. The light quantity adjusting switches 112 are constituted of four slide levers for independently adjusting the light quantity of each of red light (R), green light (G), blue light (B), and violet light (V).

The initial setting mode after activation of the endoscope is basically the white light mode, so an observation image in the white light mode is projected on the monitor 100.

Here, the modes can be switched with a given timing by an observer during observation. Switching is conducted by selecting any of the white light mode, the special light mode, and hybrid modes 1 and 2 by pressing any button of the observation mode selecting switches 111 mounted on the input unit 110.

The initial setting mode after activation of the endoscope can be changed by the input keys 113 mounted on the input unit 110. Information inputted by the input keys 113 is displayed on the display panel 114, so an input value can easily be confirmed.

The observation mode selecting switches 111 may be mounted on a scope. The scope will be described later.

Next, the operations of the hybrid mode will be explained.

For example, when an observer wishes to confirm information on superficial blood vessels in addition to a surface profile during observation in the white light mode, the observer selects the hybrid mode by the observation mode selecting switches 111. Here, a selected hybrid mode is temporarily set as the hybrid mode 1. After the selection, as shown in FIG. 8, an image in the hybrid mode 1 appears on the monitor 100. The light quantity of each color in the hybrid mode 1 is a given spectral pattern value set in advance.

The observer first confirms an image in the hybrid mode 1 illuminated by a spectral pattern set in advance on the monitor 100. The observer, after that, adjusts the light quantity so as to obtain a desired image, watching the monitor 100. Light quantity modulation is conducted by the observer by operating the slide levers of the light quantity adjusting switches 112 mounted on the input unit 110 so as to make a desired color tone while watching the monitor 100.

The light quantity modulation by the light quantity adjusting switches 112 are basically conducted by changing the intensity with an arbitrary step width, and may also be conducted by continuously changing the intensity.

Please note that the light quantity adjusting switches 112 may be mounted on the scope.

The setting value of a spectral pattern in the hybrid mode can be changed by the input keys 113 mounted on the input unit 110. Information inputted by the input keys 113 is displayed on the display panel 114, so an input value can easily be confirmed.

In addition, an observer can not only switch an observation mode with a given timing but can also display observation images in given modes on the monitor 100 at the same time.

Figure 9:
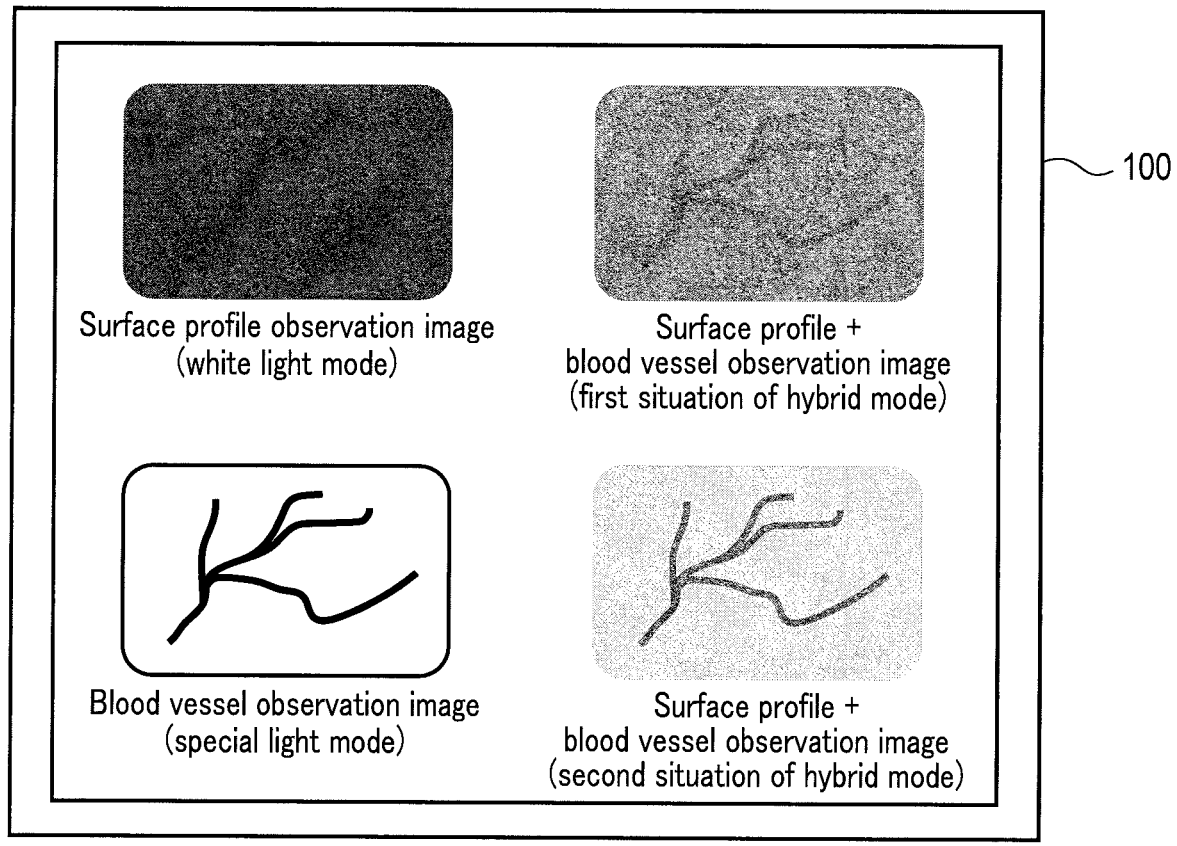
FIG. 9 shows display images on a monitor in the white light mode, the special light mode, and first and second situations in the hybrid mode, respectively.

For example, at the time of switching to the hybrid mode 1 after observation in the white light mode, in addition to an observation image in the hybrid mode 1, an observation image in the white light mode may also be continuously displayed on the monitor 100. Furthermore, as shown in FIG. 9, in addition to observation images in the white light mode and the hybrid mode 1, observation images in the hybrid mode 2 and the special light mode, i.e. observation images in up to four modes may be displayed on the monitor 100 at the same time. In addition, observation images in the four modes may be displayed on the monitor 100 sequentially.

In addition, regarding display of an observation image in each mode, observation images in all the modes may be displayed on the monitor 100 in real time; alternatively, only an observation image in an arbitrary mode may be displayed by real-time display, while observation images in other modes are displayed by still image display.

When observation images in modes are displayed on the monitor 100, it is possible by the input unit 110 to input the selection of modes to be displayed, or input the setting of display requirements for each mode, such as "constant real-time display" and "still image display other than given designated modes."

As has been explained, by the special light endoscope 200 in the present embodiment, in addition to observation in the white light mode and the special light mode, observation in the hybrid mode is possible. This makes it possible to obtain images of both screening with a certain level of image quality and blood vessel observation. Thus, an image appropriate for screening can be obtained at high speed. Because of this, it can be expected that the oversight of a lesion at the time of screening will be reduced.

Here, an example of the light quantity percentage of each color light in the hybrid mode is shown, but is not limited to this; values made by appropriately adjusting the light quantity percentage of each color light according to the situation or environment of a subject may be used.

Also, the light quantity of each color in the hybrid mode may be continuously changed. This makes it possible to, for example, seamlessly change the spectral pattern of white light to the spectral pattern of special light. Besides, the light quantity of each color in the hybrid mode may be changed at one's discretion. This makes it possible to achieve screening and easy vascular abnormality observation at the same time under rough magnification or under medium magnification that is not very high, thereby increasing the probability of the identification of a lesion.

Figure 10:
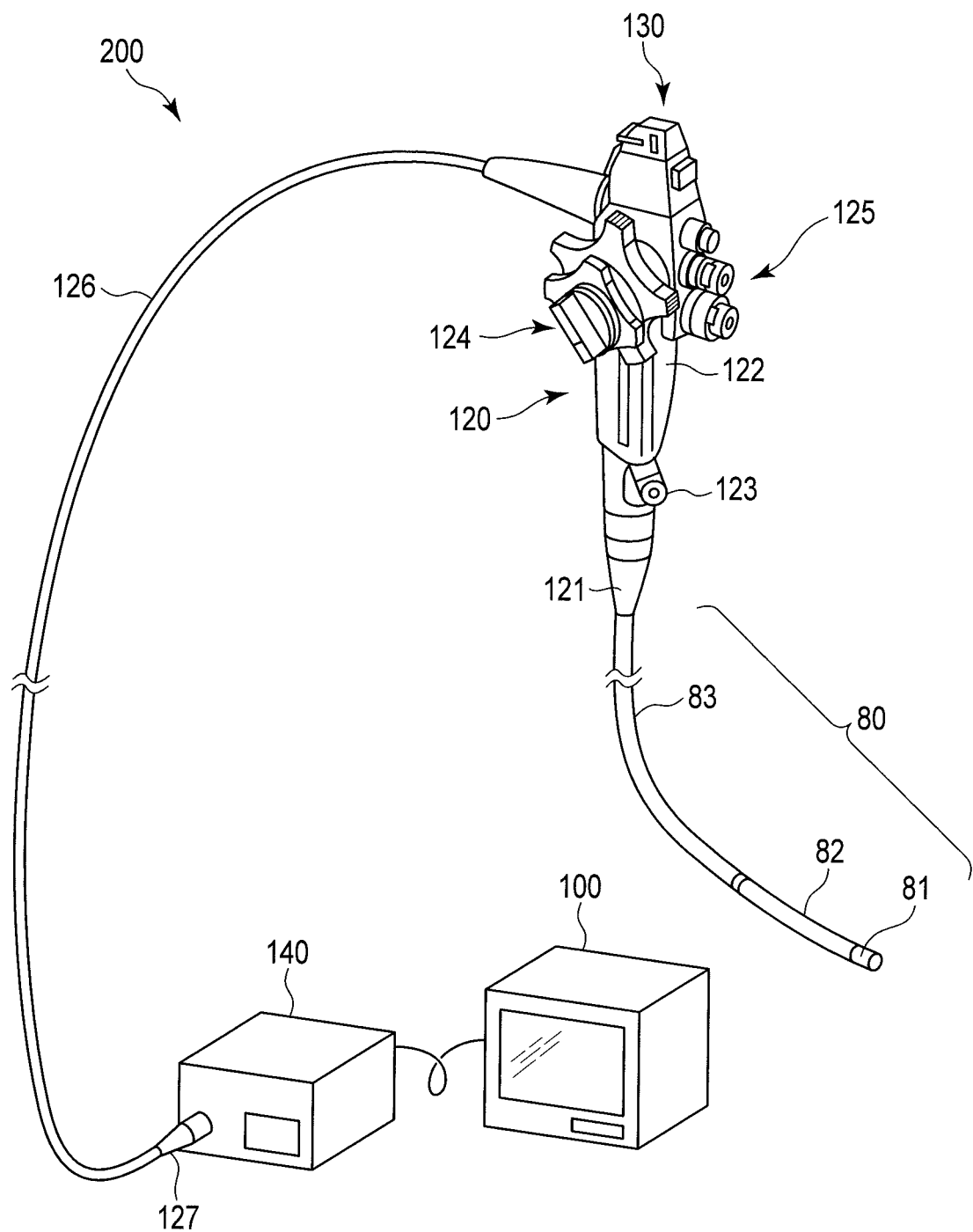
FIG. 10 shows a specific configuration example of a special light endoscope shown in FIG. 1.

FIG. 10 shows a specific configuration example of the special light endoscope 200 shown in FIG. 1. The special light endoscope 200 includes a scope 130, a main unit 140 to be connected to the scope 130, and the monitor 100 to be connected to the main unit 140. The main unit 140 may include the light source apparatus 70, the image processing apparatus 90, and the input unit 110.

The scope 130 includes the flexible insertion portion 80 to be inserted into a subject including an observation object, and an operation portion 120 connected to the base end of the insertion portion 80. The insertion portion 80 is a long and thin tubular portion on the tip of the scope, and includes a hard end portion 81, a bendable portion 82 connected to the base end of the hard end portion 81, and a flexible tube 83 connected to the base end of the bendable portion 82. In the hard end portion 81, the aforesaid imager 50 or the diffuser 40 is embedded. The bendable portion 82 is bendable in a desired direction by operating the operation portion 120. The flexible tube 83 is bendable, and is, for example, bendable along with the bend shape of a subject.

The operation portion 120 includes a bend stopper 121 connected to the base end of the flexible tube 83, and a holder 122 connected to the base end of the bend stopper 121. In the bend stopper 121, a tool insertion port 123 leading to an insertion channel extending in the insertion portion 80 is provided. The holder 122 includes a bend operation dial 124 for bend-operating the bendable portion 82, and switches 125 for conducting air-supplying, water-supplying, aspirating, photographing, etc.

In the insertion portion 80 and the operation portion 120, the optical fiber 23 whose tip is connected to the diffuser 40, and the image cable 51 whose tip is connected to the imager 50, extend. The optical fiber 23 and the image cable 51 laterally extend from the base end of the holder 122, and constitute a universal cord 126. At the base end of the universal cord 126, a connector 127 is provided. The connector 127 is connected to the main unit 140 in a detachable manner.

In the configuration example of FIG. 10, the scope 130 includes the insertion portion 80 and the operation portion 120, but may be a structure including at least the insertion portion 80. In other words, the scope 130 is, in a broad sense, a structure including the insertion portion 80, and in a narrow sense, may be a structure including the insertion portion 80 and the operation portion 120. The scope 130 may include the universal cord 126, in addition to the insertion portion 80 and the operation portion 120.

The switches 125 of the operation portion 120 may include the aforesaid observation mode selecting switches 111 or light quantity adjusting switches 112.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
an endoscope having an image sensor configured to image an observation object;
a light source configured to provide illumination light to be emitted from an end portion of the endoscope such that the image sensor images the observation object illuminated by the illumination light, the light source comprising a plurality of narrow band light sources configured to emit narrow band light;
observation mode selecting switches configured to select an illumination mode from at least a white light mode, a special light mode, and a hybrid light mode; and
a controller configured to:
receive a signal from the observation mode selecting switches indicating selection of the illumination mode from at least the white light mode, the special light mode, and the hybrid light mode;
when the special light mode is selected, control the light source to provide the illumination light that includes at least first and second narrow band light of the plurality of light sources, a color of the first narrow band light being different from a color of the second narrow band light; and
when the hybrid light mode is selected, control the light source to provide the illumination light in a spectral pattern that includes the at least first and second narrow band light included in the special light mode, a spectral pattern in the hybrid mode being different from either of a spectral pattern of illumination light in the white light mode and a spectral pattern of illumination light in the special light mode.

2. The endoscope system according to claim 1, wherein the controller controls the light source, in the hybrid mode, to selectively provide illumination light having a first spectral pattern close to the spectral pattern of illumination light in the white light mode, and to provide illumination light having a second spectral pattern close to the spectral pattern of illumination light in the special light mode.

3. The endoscope system according to claim 2, wherein the second spectral pattern retains a color tone almost equal to a color tone of the first spectral pattern, and differs from the first spectral pattern in the light quantity of each narrow band light except in a visible light region.

4. The endoscope system according to claim 1, wherein the controller controls the light source, in the hybrid mode, to provide illumination light including a narrow band light included in common in illumination light in the white light mode and illumination light in the special light mode, and
wherein the light quantity of the narrow band light included in common is the light quantity between the light quantity of each narrow band light of illumination light in the white light mode and the light quantity of each narrow band light of illumination light in the special light mode.

5. The endoscope system according to claim 1, wherein the controller controls the light source, in the hybrid mode, to provide illumination light that has the light quantity between the light quantity of each narrow band light of illumination light in the white light mode and the light quantity of each narrow band light of illumination light in the special light mode.

6. The endoscope system according to claim 1, wherein the controller controls the light source, in the hybrid mode, to provide illumination light comprising narrow band lights that each have the light quantity of an average of the light quantity of each narrow band light of illumination light in the white light mode and the light quantity of each narrow band light of illumination light in the special light mode.

7. The endoscope system according to claim 1, wherein the controller controls the light source in the hybrid mode to provide illumination light in which the light quantity of a narrow band light in a bluish-violet region of 380 through 500 nm in wavelength is large compared to illumination light in the white light mode and that retains a color tone closer to illumination light in the white light mode than to illumination light in the special light mode.

8. The endoscope system according to claim 7, wherein the controller controls the light source in the hybrid mode to provide illumination light in which the light quantity of a narrow band light in a bluish-violet region of 380 through 500 nm in wavelength is large compared to illumination light in the white light mode and that retains a color tone almost equal to illumination light in the white light mode.

9. The endoscope system according to claim 1, wherein the controller controls the light source in the hybrid mode to provide illumination light in which the light quantity of a narrow band light in a greenish-yellow region of 500 through 570 nm in wavelength is large compared to illumination light in the white light mode and that retains a color tone almost equal to illumination light in the white light mode.

10. The endoscope system according to claim 1, wherein the controller:
controls the light source in the special light mode to provide illumination light that includes at least a narrow band light in at least each of a wavelength region of 380 through 445 nm and a wavelength region of 510 through 550 nm, and
controls the light source in the white light mode to provide illumination light that includes at least a narrow band light in at least each of a wavelength region of 380 through 500 nm, a wavelength region of 500 through 570 nm, and a wavelength region of 570 through 700 nm.

11. The endoscope system according to claim 1, wherein the controller controls the light source, in the special light mode, to provide illumination light that includes at least a narrow band light in at least each of a wavelength region of 390 through 445 nm that is violet, and a wavelength region of 530 through 550 nm that is green.

12. The endoscope system according to claim 1, further comprising a display,
wherein the light source selectively provides illumination light in the white light mode, illumination light in the special light mode, and illumination light in the hybrid mode, and
wherein the controller controls the display to display at least two of an image in the white light mode, an image in the special light mode, and an image in the hybrid mode on the display simultaneously or sequentially.

13. The endoscope system according to claim 1, wherein the plurality of narrow band light sources including a blue light source to emit blue light, a red light source to emit red light, a green light source to emit green light and a violet light source to emit violet light; and
the light source further comprising an optical coupler configured to combine the illumination light emitted by the plurality of narrow band light sources.

14. The endoscope system according to claim 13, wherein the controller:
controls the light source in the white light mode to provide illumination light that includes each of at least two of the red light, the green light, and the blue light,
controls the light source in the special light mode to provide illumination light that includes at least each of the green light and the violet light, and
controls the light source in the hybrid mode to provide illumination light that includes at least each of the green light, the red light, the blue light and the violet light and in which the light quantity of each of the green light, the red light, the blue light and the violet light other than the green light, the red light, the blue light and the violet light included in illumination light in the special light mode is large compared to the special light mode.

15. The endoscope system according to claim 14, wherein the controller:
controls the light source in the white light mode to provide illumination light that includes at least each of the red light, the green light, and the blue light,
controls the light source in the special light mode to provide illumination light that includes at least each of the green light and the violet light, and
controls the light source in the hybrid mode to provide illumination light that includes at least each of the green light, the red light, the blue light and the violet light and in which the light quantity of each of the green light, the red light, the blue light and the violet light not included in illumination light in the special light mode is enhanced.

16. The endoscope system according to claim 13, further comprising a light quantity output adjuster switch corresponding to each of the blue light source, the red light source, the green light source and the violet light source to control a light quantity emitted by of each of the blue light source, the red light source, the green light source and the violet light source.

17. The endoscope system according to claim 16, wherein the controller controls the illuminator in the hybrid mode based on an output of the light quantity output adjuster switches to adjust the light quantity of a narrow band light in a yellowish-red region so as to maintain the color tone.

18. The endoscope system according to claim 16, wherein the controller controls the light source in the hybrid mode based on an output of the light quantity output adjuster switches to adjust the light quantity of a narrow band light in each of red and blue regions so as to maintain the color tone.

19. The endoscope system according to claim 1, wherein the light source only consists of the plurality of narrow band lights sources.

20. The endoscope system according to claim 1, wherein the illumination light in the hybrid mode includes all narrow band lights in the white light mode and further includes all narrow band lights included in the special light mode.

21. A light source for use with an endoscope, the light source comprising:
   a plurality of narrow band light sources configured to emit narrow band light;
   a controller configured to:
      receive a signal for switching the illumination light to a white light mode, a special light mode, and a hybrid mode;
      control the light source in the special light mode to provide the illumination light that includes at least first and second narrow band light of the plurality of light sources, a color of the first narrow band light being different from a color of the second narrow band light; and
      control the light source in the hybrid mode to provide the illumination light in a spectral pattern that includes the at least first and second narrow band light included in the special light mode, a spectral pattern in the hybrid mode being different from either of a spectral pattern of illumination light in the white light mode and a spectral pattern of illumination light in the special light mode.

* * * * *